United States Patent [19]
Chapurlat

[11] 3,935,272
[45] Jan. 27, 1976

[54] PROCESS FOR THE OXIDATION OF OLEFINE COMPOUNDS

[75] Inventor: Robert Chapurlat, Rhone, France

[73] Assignee: Rhone-Poulenc S.A., Paris, France

[22] Filed: May 2, 1972

[21] Appl. No.: 249,510

[30] Foreign Application Priority Data
May 3, 1971  France .................. 71.15774

[52] U.S. Cl.... 260/597 R; 260/348.5; 260/348.5 L; 252/469
[51] Int. Cl.² .......................................... C07C 45/04
[58] Field of Search ............... 260/597 R, 597 B

[56] References Cited
UNITED STATES PATENTS

| | | | |
|---|---|---|---|
| 1,999,620 | 4/1935 | Van Peski et al. | 260/597 R |
| 3,133,968 | 5/1964 | Kummer | 260/597 R |
| 3,259,638 | 7/1966 | Allison | 260/597 R |

*Primary Examiner*—James O. Thomas, Jr.
*Assistant Examiner*—James H. Reamer
*Attorney, Agent, or Firm*—Stevens, Davis, Miller & Mosher

[57] ABSTRACT

Olefines of at least 3 carbon atoms are oxidised e.g. to ketones or epoxy compounds using, as oxidising agent, uranium oxide, hafnium oxide or an oxo-metal compound of formula

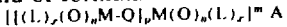
$[[(L)_x(Q)_n M-Q]_p M(O)_n(L)_x]^m A$ in which M represents Ti, Zr, Hf, V, Nb, Ta, Mo, W or U, L represents a monodentate or polydentate ligand, A represents an organic or inorganic anion or cation, Q represents oxygen or sulphur, $x$ is an integer greater than or equal to zero, $p$ is equal to zero or one, $m$ is a positive or negative integer and there is one or more oxygen atoms directly bonded to the metal and not bonded to an organic radical.

Typical oxidants are vanadyl-, zirconyl-, titanyl-, molybdyl-, tungstyl- and uranyl-acetylacetonate.

15 Claims, No Drawings

PROCESS FOR THE OXIDATION OF OLEFINE COMPOUNDS

The present invention relates to a process for the oxidation, using metal derivatives, of olefinic compounds containing at least three carbon atoms to oxygen containing compounds.

It has already been proposed to oxidise olefines such as ethylene, propylene, cyclohexene and styrene, by metal ions, in the presence of compounds which provide oxygen, such as water, alcohols or carboxylic acids. Thus, oxidation of ethylene by palladium-(II) chloride, in the presence of water or a carboxylic acid, gives acetaldehyde or vinyl esters respectively; if propylene is subjected to oxidation by palladium-(II) chloride in the presence of water, acetone is formed (cf. R. F. GOULD Homogeneous Catalysis, chapter 6, pages 126 et seq. KIRK-OTHMER, Encyclopedia of Chemical Technology, 16, page 586). It has also been proposed to oxidise olefines such as ethylene, propylene, butene, hexene and styrene to oxygen-containing derivatives such as aldehydes, ketones, glycols, ketals and glycol esters, using the thallic ion as the oxidising agent and by working in an alcohol (methanol), a carboxylic acid (acetic acid or propionic acid) or in water (cf. R. R. GRINSTEAD, J. Org. Chem., 26, 238–40 (1961); H. J. KABBE, Ann., 656, 204–21, (1962); U.S. Pat. Nos. 3,048,636 and 3,452,047). In these various processes, it is generally accepted that an intermediate organometallic compound is formed which reacts thereafter with the water, the alcohols or the carboxylic acids.

The present invention provides a process for the production of an oxygen containing organic compound by oxidising an olefinic compound containing at least three carbon atoms and at least one aliphatic carbon-carbon double bond using as oxidising agent, uranium oxide, hafnium oxide or an oxo-metal compound of the general formula:

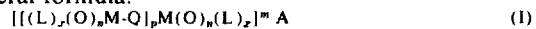

$$[[(L)_y(O)_xM-Q]_pM(O)_n(L)_z]^m A \quad (I)$$

in which M represents Ti, Zr, Hf, V, Nb, Ta, Mo, W or U, L represents a monodentate or polydentate ligand, A represents an organic or inorganic anion or cation, Q represents oxygen or sulphur, x is an integer greater than or equal to zero, p is equal to zero or one, m is a positive or negative integer and there is one or more oxygen atoms directly bonded to the metal and not bonded to an organic radical.

The oxidising agent of formula (I) can be a salt derived from an oxo-cation or from an oxo-anion depending on whether m represents a positive or negative integer. A preferred class of oxidising agent consists of the derivatives of oxo-cations of the general formula (I) in which m is a positive number and particularly those in which x is equal to zero. In this case, the oxo-cation corresponds to the general formula:

$$[(M(O_n)-Q)_zM(O)_n]^{z+} \quad (II)$$

in which z is an integer greater than or equal to 1. The associated ion A then may represent the anion of an inorganic or organic Bronstedt acid which forms a salt, which may or may not be chelated, with the oxo-cation of the formula (II).

Oxo-cations of the formula (II) which may be used in the present invention include titanyl ($TiO^{2+}$), molybdyl ($MoO_2^{2+}$), molybdenyl ($MoO^{3+}$), tungstyl ($WO_2^{2+}$), vanadyl ($VO^{2+}$), zirconyl ($ZrO^{2+}$), uranyl ($UO^{2+}$), hafnyl ($HfO^{2+}$), vanadic ($VO^{3+}$), ($TaO^{3+}$), $TaO_2^+$) and $NbO_3^+$) ions.

Anions A which are capable of forming salts with the oxo-cations of the formula (II) include inorganic anions such as halide (chloride, bromide and fluoride), nitrate, phosphate or sulphate, or organic anions derived from monocarboxylic or polycarboxylic acids or from compounds which can yield one or more protons H$^+$, such as alcohols, phenols or β-dicarbonyl compounds or their enolisable derivatives. Carboxylic acids from which the anions may be derived include saturated or unsaturated aliphatic acids, cycloaliphatic acids or aromatic acids, such as formic, acetic, propionic, hexanoic, decanoic, lauric, palmitic, stearic, eicosenoic, naphthenic, oxalic, adipic, cyclohexanecarboxylic, benzoic, toluic and phthalic acids. Of the compounds capable of yielding hydrogen as a proton, β-dicarbonyl compounds which form a chelate with the oxocations of the formula (II) are preferentially used. Examples of such β-dicarbonyl compounds are β-ketoesters (ethyl acetoacetate, methyl acetoacetate or methyl benzoylacetate) and β-diketones (or the diimines which they form with diamines such as ethylenediamine), such as acetylacetone, 2,4-hexanedione, 2,4-heptanedione, 5-methyl-2,4-hexanedione, 5-methoxy-2,4-pentanedione, 3,5-heptanedione, 1,1,1-trifluoro-2,4-pentanedione, benzoylacetone, dibenzoylmethane, o-methoxybenzoylacetone, 1,1,1-trifluoro-3-benzoylacetone, 1,3-cyclopentanedione, 1,3-cyclohexanedione, 5,5-di-methyl-1,3-cyclohexanedione, 2-acetylcyclohexanone, 1-hydroxybenzoylacetone and bis-(acetylacetone)-ethylenediimine.

Examples of oxidising compounds of formula I in which the oxo-cation corresponds to the formula (II), which can be used in the invention include titanyl chloride, titanyl nitrate, zirconyl sulphate, uranyl nitrate, zirconyl chloride, zirconyl formate, zirconyl acetate, zirconyl laurate zirconyl palmitate, zirconyl stearate, zirconyl oleate, vanadyl acetate, vanadyl benzoate, vanadyl naphthenate, vanadyl oxalate, molybdenyl oxalate, titanyl acetylacetonate, vanadyl acetylacetonate, molybdyl acetylacetonate, molbdenyl acetylacetonate, tungstyl acetylacetonate, uranyl acetylacetonate, vanadyl benzoylacetonate, bis-(dipivaloylmethane)-oxovanadium, zirconyl acetylacetonate, uranyl benzoylacetonate, uranyl 1,1,1-trifluoro-acetylacetonate and bis-(acetylacetone)-ethylenediiminooxovanadium.

If m is a negative integer, the oxidising compound of formula (I) is a derivative an oxo-anion. In this case, A is an inorganic cation which may be derived from an alkali metal or alkaline-earth metal or from one of the metals designated by M in the formula (I). Specific examples of compounds of the formula (I) derived from oxo-anions which can be used in the invention include alkali metal titanates (e.g. $Li_2TiO_3$ and $Na_2TiO_3$), alkalineearth metal titanates (e.g. $CaTiO_3$), alkali metal zirconates (e.g. $Li_2ZrO_3$, $Na_2ZrO_3$ and $K_2ZrO_3$), zirconium molybdate ($ZrO_2 \cdot 2 MoO_3$), zirconium tungstate ($[ZrO_2]_5 \cdot [WO_3]_9$), and ortho-vanadates and meta-vanadates such as sodium ortho-vanadate $Na_3VO_4$, zirconium meta-vanadate ($Zr(VO_3)_4$) and uranium meta-vanadate ($UO_2(VO_3)_2$).

The ligands (L) in formula (I) can be chosen from amongst the organic compounds containing one or more groups which are donors of electron pairs, such as carbon-carbon double bonds, nitrile, ether, thioether, alcohol, thioalcohol, phenol, amine, imine, oxime, hydroxylamine, aldehyde, arsine, phosphine and stibine groups, and the nitrogen atoms of heterocyclic bases. Suitable ligands L include diolefines, such as butadiene or cyclopentadiene; nitriles such as propionitrile or acrylonitrile; phosphines such as trimethylphosphine; heterocyclic bases such as 1,10-phenanthroline, 2,2'-dipyridyl, pyridylimidazole, 2-pyridylimidazoline or hydroxyquinoline; diamines (e.g. ethylenediamine); aminoalcohols; phosphines or diarsines; phenols such as catechol; and hydroxyacids such as salicylic acid.

Examples of oxidising compounds of the formula (I) comprising a ligand L include derivatives of oxo-cations such as cyclopentadienyl-oxomolybdenum dichloride [$(C_5H_5)Mo(O)Cl_2$]; cyclopentadienyl-oxomolybdenum chloride [$(C_5H_5)MoO_2Cl_2$]; derivatives of oxo-anions such as ammonium vanadyl-(orthohydroxybenzoate) or sodium vanadyl-(orthohydroxybenzoate) [$[VO(O—C_6H_4—COO)_2]Na_2$]; ammonium oxoniobium-catecholate [$NbO(OH—C_6H_4-O)_3(NH_4)_3$]; and potassium molybdenyl-catecholate [$MoO(HO—C_6H_4—O)_3K_3$].

The olefines which can be oxidised by the process according to the present invention are compounds containing one or more aliphatic carbon-carbon double bonds. More specifically, olefine compounds of the general formula:

(III)

in which R is a hydrocarbon radical containing 1 to 30 carbon atoms, which may be or may not be saturated and which may or may not be substituted by functional groups, and $R_1$, $R_2$ and $R_3$ represent hydrogen or hydrocarbon radicals which may be the same as or different from R, $R_2$ or $R_3$ being able to form an unsaturated hydrocarbon ring with R or $R_1$, can be subjected to oxidation by the oxomellic derivatives of formula (I).

Still more specifically, R can be a linear or branched alkyl radical such as methyl, ethyl, propyl, isopropyl, isobutyl, hexyl, or decyl; an alkenyl radical such as ethenyl or propenyl; a cycloalkyl or cycloalkenyl radical (e.g. cyclohexyl or cyclohexenyl); an aryl radical such as phenyl, an aralkyl radical such as toluyl, an alkylaryl radical such as benzyl or phenylethyl, or an alkenylaryl radical such as vinylphenyl; or an alkyl, cycloalkyl or aryl radical substituted by functional groups such as hydroxy, carboxyl, alkoxycarbonyl, carbonyloxalkyl, aldehyde, ketone, nitrile, amide or amine groups or halogen atoms (e.g. chlorine or bromine).

Examples of compounds which can be oxidised by the process of the invention include propylene, 1-butene, 2-butene, isobutene, 1-pentene, 2-pentene, 1-hexene, 1-decene, the dodecenes, butadiene, 2-methylbutadiene, cyclohexene, cyclobutadiene, vinylcyclohexane, cyclohexene, styrene, divinylbenzene, the methylstyrenes and unsaturated fatty acids and their esters or amides, such as linoleic, oleic, ricinoleic and palmitoleic acid.

The exact nature of the products produced vary according to the compounds subjected to the oxidation. Thus, acetone is produced, by oxidising propylene, and by oxidising olefines higher than propylene, the corresponding oxides are principally produced.

The temperature of the reaction can vary within wide limits depending on the nature of the olefine compound and of the oxidising agent. Usually, the reaction is carried out at temperatures of between 20 and 300°C, and the pressure can be greater than or equal to atmospheric pressure.

The oxidation reaction by the oxo-metallic compounds can be carried out in the liquid phase or in the gas phase. If the reaction is carried out in the liquid phase, it can be carried out either in the absence or in the presence of a solvent which is inert under the reaction conditions.

A saturated aliphatic hydrocarbon (e.g. hexane, pentane or cyclohexane), an aromatic hydrocarbon (e.g. benzene, toluene or xylene), a halogenated hydrocarbon (e.g. 1,2-dichloroethane, chlorobenzene or chlorotoluene) or a polar solvent such as a nitrile (e.g. acetonitrile), an amide (e.g. dimethylformamide or hexamethylphosphotriamide) or an ether (e.g. tetrahydrofurane) are very suitable. The organic solvent can optionally contain a small amount of water which can be present in an amount of up to 5% by weight. If the oxidation is carried out in the absence of an organic solvent, conditions of temperature and pressure are chosen such that the olefine remains in the liquid state. In either case, the oxidising agent can be either in solution or in suspension in the reaction medium.

If the reaction is carried out in the gas phase, the olefine compound is passed over the solid oxidising agent using the usual methods of contact of gases and solids. Thus the olefine compound, raised to the suitable temperature, can be passed over a fluidised bed of the oxidising compound. The gaseous olefine compound can also be passed through a column containing the solid oxidising agent in a stationary phase. The oxidant can be deposited on a support which is inert under the reaction conditions such as alumina, silica, aluminium silicates, pumice stone, diatomaceous earths and charcoals.

After an oxidation reaction, the oxidising compound can be regenerated by treatment with oxygen or with a gas containing oxygen, such as air, and can be used for a new reaction.

The Examples which follow illustrate the invention and show how it can be put into practice.

EXAMPLES 1 to 21

10 G of oxidising agent, 80 cm³ of a solvent and 20 g of olefine compound are introduced into a 250 cm³ stainless steel autoclave purged with nitrogen. The contents of the autoclave are brought to the requisite temperature for varying time intervals, at the autogenic pressure. The autoclave is then cooled, the olefine compound is degassed if necessary and then the residue is subjected to a chromatographic analysis. The results obtained are given in the following table:

| Example | Oxidising Agent | Olefine compound | Solvent | T °C | Time in hours | Products obtained | |
|---|---|---|---|---|---|---|---|
| | | | | | | Nature | Yield relative to the oxidising agent introduced |
| 1 | Vanadyl acetylacetonate | Propylene | Dimethylformamide | 130 | 20 | Acetone | 76% |

| Example | Oxidising Agent | Olefine compound | Solvent | T °C | Time in hours | Products obtained | |
|---|---|---|---|---|---|---|---|
| | | | | | | Nature | Yield relative to the oxidising agent introduced |
| 2 | ditto | ditto | Tetrahydrofurane | " | " | " | 45% |
| 3 | ditto | ditto | HMPT** | " | " | " | 100% |
| 4 | ditto | ditto | Acetonitrile | " | " | " | 91% |
| 5 | ditto | ditto | 1,2-Dichloro-ethane | " | " | " | 21% |
| 6 | ditto | ditto | Chlorobenzene | " | " | " | 35% |
| 7 | ditto | ditto | Chlorobenzene/water (1%) | " | 18 | " | 100% |
| 8 | Vanadyl benzoylacetonate | ditto | Chlorobenzene | " | 20 | " | 21% |
| 9 | Bis-(dipivaloylmethane)-oxovanadium | ditto | " | " | " | " | 95% |
| 10 | Bis-(acetylacetone)-ethylene-diimino-oxovanadium | ditto | " | " | " | " | 61% |
| 11 | Zirconyl acetonylacetonate | ditto | " | " | " | " | 60% |
| 12 | Titanyl acetylacetonate | ditto | " | " | " | " | 60% |
| 13 | Molybdyl acetylacetonate $(C_5H_7O_2)_2MoO_2$ | ditto | Benzene | " | " | " | 30%* |
| 14 | Molbdenyl acetylacetonate $[(C_5H_7O_2)_2MoO]_2O$ | ditto | Chlorobenzene | " | " | " | 20%* |
| 15 | Tungstyl acetylacetonate | ditto | " | " | " | " | 100%* |
| 16 | Uranyl acetylacetonate | ditto | " | " | " | " | 140%* |
| 17 | Hafnium oxide (HfO₂) | ditto | " | " | " | " | 40%* |
| 18 | Uranium oxide (UO₃) | ditto | " | " | " | " | 40%* |
| 19 | Vanadyl acetylacetonate | 1-Butene | " | 180 | " | 1,2-Epoxy-butane | 60% |
| 20 | Uranyl acetylacetonate | ditto | " | 130 | " | " | 120%* |
| 21 | Uranyl acetylacetonate | 2-Butene | " | " | " | 2,3-Epoxy-butane | 160% |

*Relative to one oxygen atom present in the metal compound
**Hexamethylphosphotriamide

EXAMPLE 22

A glass column 30 cm high and 8 mm in diameter is packed with 30 cm³ (25 g) of alumina of average particle size 500 μ impregnated with vanadyl acetylacetonate (content 2.64% by weight). The amount of vanadyl acetylacetonate used in this way represents $2.3 \times 10^{-3}$ mol (that is to say 0.609 g). The contents of the column are brought to and held at 130°C and then a mixture of propylene/nitrogen (50% nitrogen by volume) is passed through the column, at a flow rate of 3 l/hour measured under normal conditions of pressure and temperature, for a period of 6 hours. The gases coming out of the column bubble into an aqueous solution of semicarbazide hydrochloride. The semicarbazone obtained, namely 0.266 g (melting point 190°C), which corresponds to the formation of $2.2 \times 10^{-3}$ mol of acetone, is isolated; the yield relative to the oxygen bonded to the vanadium in the vanadyl acetylacetonate is thus 100 %.

The oxidising agent deposited on alumina was prepared by impregnating, over a period of 3 hours, 30 cm³ of alumina with 100 cm³ of a solution containing 1% by weight of vanadyl acetylacetonate in 1,2-dichloroethane, filtering and then evaporating the residual solvent at 80°C under a reduced pressure of 1 mm of mercury (duration 3 hours).

EXAMPLES 23 to 36

The procedure according to Example 22 is followed, whilst changing the nature of the oxidising agent, the length of time for which the olefine compound is passed, the nature of the latter and the temperature. The results are given in the following table:

| Ex. | OXIDISING AGENT | T°C | Time in hours | Olefine Compounds | Products obtained |
|---|---|---|---|---|---|
| 23 | Bis-(acetylacetone)-ethylenediimino-oxovanadium | 130 | 7 | Propylene | Acetone |
| 24 | Titanyl acetylacetonate | " | " | " | " |
| 25 | Zirconyl acetylacetonate | " | " | " | " |
| 26 | Molybdyl acetylacetonate $(C_5H_7O_2)_2MoO_2$ | " | 1 hour 15 minutes | " | " |
| 27 | Molybdenyl acetylacetonate $[(C_5H_7O_2)_2MoO]_2O$ | " | 7 | " | " |
| 28 | Tungstyl acetylacetonate | " | 8 | " | " |
| 29 | Uranyl acetylacetonate | 80 | 17 | " | " |
| 30 | Uranium oxide (UO₃)* | 130 | 6 | " | " |
| 31 | Vanadyl acetylacetonate | 180 | " | Cyclohexene** | Epoxycyclohexane |
| 32 | Molybdyl acetylacetonate | " | " | " | " |
| 33 | Molybdenyl acetylacetonate | " | " | " | " |
| 34 | Molybdyl acetylacetonate | " | " | 1-Hexene** | 1,2-Epoxyhexane |
| 35 | Uranyl acetylacetonate | 130 | " | 1-Butene | 1,2-Epoxybutane |
| 36 | Tungstyl acetylacetonate | " | " | 2-Butane | 2,3-Epoxybutane |

*The oxidising agent is produced by impregnating 30 g of alumina with an aqueous solution containing 40% by weight of uranyl nitrate, filtering and drying for 10 minutes at 80°C and then treating with air at 500°C for 15 hours.
**For these two olefines, the apparatus used consists of a flask equipped with a heating device and to which the column containing the oxidising agent is fixed. The mixture of vapours coming from the column is condensed and the condensate is returned to the flask.

I claim:

1. Process for the production of acetone by oxidising propylene in an oxygen-free atmosphere, in the gas phase, in the absence of water or in the presence of up to 5% by weight of water, using, as oxidising agent, an oxy-metal compound containing one or more oxygen atoms directly bonded to the metal and not bonded to an organic radical, selected from an oxo-metal compound of the general formula:

$$[[(L)_x(O)_n M-Q]_p M(O)_n(L)_r]^m A \quad (I)$$

in which M represents V, L represents a monodentate or polydentate ligand, A represents an organic or inorganic anion or cation, Q represents oxygen or sulphur, $x$ is an integer greater than or equal to zero, $p$ is equal to zero or one, $m$ is a positive or negative integer and $n$ is an integer greater than or equal to zero such that there is one or more oxygen atoms directly bonded to the metal and not bonded to an organic radical.

2. Process for the production of acetone by oxidising propylene in an oxygen-free atmosphere, in the gas phase, in the absence of water or in the presence of up to 5% by weight of water, using, as oxidizing agent, an oxy-metal compound containing one or more oxygen atoms directly bonded to the metal and not bonded to an organic radical, selected from uranium oxide, hafnium oxide an oxo-metal compound of the general formula:

$$[[(L)_x(O)_n M-Q]_p M(O)_n(L)_r]^m A \quad (I)$$

in which M represents Ti, Zr, Hf, V, Nb, Ta, Mo, W or U, L represents a monodentate or polydentate ligand, A represents an organic or inorganic anion or cation, Q represents oxygen or sulphur, $x$ is an integer greater than or equal to zero, $p$ is equal to zero or one, $m$ is a positive or negative integer and $n$ is an integer greater than or equal to zero such that there is one or more oxygen atoms directly bonded to the metal and not bonded to an organic radical.

3. Process according to claim 1 wherein the oxidising agent is a compound of formula (I) in which $x$ is equal to zero, $m$ is a positive integer and A represents an inorganic or organic anion which forms a salt which may be chelated with the oxo-metal cation.

4. Process according to claim 3, wherein the oxidising agent is a compound of formula (I) which is a salt of a monocarboxylic or polycarboxylic acid, a β-diketonate or diketimine-diketonate.

5. Process according to claim 4 wherein the oxidising agent is a tungstyl-, vanadyl-, molybdyl-, molybdenyl-zirconyl-, titanyl-, uranyl- or hafnyl-β-diketonate.

6. Process according to claim 5 wherein the oxidising agent is a tungstyl-, vanadyl-, molybdyl-, molybdenyl-, zirconyl-, titanyl-, uranyl- or hafnyl- acetylacetonate; a tungstyl-, vanadyl-, molybdyl-, molybdenyl-, zirconyl-, titanyl-, uranyl- or hafnyl-ethylene- diimineacetylacetone; bis-(pivaloylmethane)-oxovanadium or vanadyl benzoylacetonate.

7. Process according to claim 1 wherein the reaction is carried out at a temperature of 20° to 300°C, at atmospheric or super atmospheric pressure.

8. Process for the production of acetone by oxidising propylene in an oxygen-free atmosphere, in an organic liquid in the absence of water or in the presence of up to 5% by weight of water, using, as oxidising agent, an oxy-metal compound containing one or more oxygen atoms directly bonded to the metal and not bonded to an organic radical, selected from uranium oxide, hafnium oxide an oxo-metal compound of the general formula:

$$[[(L)_x(O)_n M-Q]_p M(O)_n(L)_r]^m A \quad (I)$$

in which M represents Ti, Zr, Hf, V, Nb, Ta, Mo, W or U, L represents a monodentate or polydentate ligand, A represents an organic or inorganic anion or cation, Q represents oxygen or sulphur, $x$ is an integer greater than or equal to zero, $p$ is equal to zero or one, $m$ is a positive or negative integer and n is an integer greater than or equal to zero such that there is one or more oxygen atoms directly bonded to the metal and not bonded to an organic radical.

9. Process for the production of acetone by oxidising propylene in an oxygen-free atmosphere, in an organic liquid in the absence of water or in the presence of up to 5% by weight of water, using, as oxidising agent, an oxy-metal compound containing one or more oxygen atoms directly bonded to the metal and not bonded to an organic radical, selected from an oxo-metal compound of the general formula:

$$[[(L)_x(O)_n M-Q]_p M(O)_n(L)_r]^m A \quad (I)$$

in which M represents V, L represents a monodentate or polydentate ligand, A represents an organic or inorganic anion or cation, Q represents oxygen or sulphur, $x$ is an integer greater than or equal to zero, $p$ is equal to zero or one, $m$ is a positive or negative integer and n is an integer greater than or equal to zero such that there is one or more oxygen atoms directly bonded to the metal and not bonded to an organic radical.

10. Process according to claim 9 wherein the oxidising agent is a compound of formula (I) in which $x$ is equal to zero, $m$ is a positive integer and A represents an inorganic or organic anion which forms a salt which may be chelated with the oxometal cation.

11. Process according to claim 10, wherein the oxidising agent is a compound of formula (I) which is a salt of a monocarboxylic or polycarboxylic acid, a β-diketonate or diketiminediketonate.

12. Process according to claim 11 wherein the oxidising agent is a tungstyl-, vanadyl-, molybdyl-, molybdenyl-, zirconyl-, titanyl-, uranyl- or hafnyl-β-diketonate.

13. process according to claim 12 wherein the oxidising agent is a tungstyl-, vanadyl-, molybdyl-, molybdenyl-, zirconyl-, titanyl-, uranyl- or hafnyl-acetylacetonate; a tungstyl-, vanadyl-, molybdyl-, molybdenyl-, zirconyl-, titanyl-, uranyl-, or hafnyl-ethylene-diimineacetylacetone; bis-(pivaloymethane)-oxovanadium or vanadyl benzoylacetonate.

14. Process according to claim 9 wherein the reaction is carried out at a temperature of 20° to 300°C., at atmospheric or super atmospheric pressure.

15. Process according to claim 9 wherein the oxidation is carried out in the presence of an organic solvent for the olefinic compound.

* * * * *